United States Patent [19]

Ostle et al.

[11] Patent Number: 5,236,708
[45] Date of Patent: Aug. 17, 1993

[54] REDUCED-PROTEIN SUBUNIT VACCINE FOR SWINE DYSENTERY

[75] Inventors: Anthony G. Ostle, Dallas Center; Michael J. Wannemuehler, Ames, both of Iowa

[73] Assignees: Iowa State University Research Foundation, Inc., Ames; Ambico, Inc., Dallas Center, both of Iowa ; a part interest

[21] Appl. No.: 430,986

[22] Filed: Nov. 3, 1989

[51] Int. Cl.$^5$ .................. A61K 39/02; A61K 39/547
[52] U.S. Cl. ........................................ 424/92; 424/88; 424/93 D; 424/94.64; 435/23; 435/220
[58] Field of Search ................. 424/88, 92, 93, 94.64; 435/220

[56] References Cited

U.S. PATENT DOCUMENTS

| | | | |
|---|---|---|---|
| 4,100,272 | 7/1978 | Glock et al. | 424/92 |
| 4,152,413 | 5/1979 | Goodnow | 424/92 |
| 4,152,414 | 5/1979 | Harris | 424/92 |
| 4,152,415 | 5/1979 | Harris | 424/92 |
| 4,203,968 | 5/1980 | Harris et al. | 424/92 |
| 4,469,672 | 9/1984 | Harris | 424/92 |
| 4,506,014 | 3/1985 | Esser et al. | 435/220 |
| 4,748,019 | 5/1988 | Lysons | 424/92 |
| 4,758,517 | 7/1988 | Parizek | 435/253 |
| 4,794,105 | 12/1988 | Hasegawa | 514/25 |
| 4,894,328 | 1/1990 | Alderete et al. | 424/92 |

FOREIGN PATENT DOCUMENTS

| | | |
|---|---|---|
| 0282965 | 9/1988 | European Pat. Off. . |
| WO85/03875 | 3/1985 | PCT Int'l Appl. . |
| WO88/04555 | 6/1988 | PCT Int'l Appl. . |
| WO85/02565 | 3/1990 | PCT Int'l Appl. . |
| 9002565 | 3/1990 | PCT Int'l Appl. . |
| 91/04036 | 4/1991 | PCT Int'l Appl. . |

OTHER PUBLICATIONS

Wannemuehler et al, "Characterization of the Major Outer Membrane Antigens of Treponema hyodysenteriae", Infection and Immunity, vol. 56, No. 12, pp. 3032-3039, Dec. 1988.

Harris, D. L., Glock, R. D., Christiansen, C. R. and Kinyon, J. M.. Vet. Med. Small Animal Clin. 67:61 (1972).

Joens, L. A. Whipp, S. C., Glock, R. D., and M. E. Neussen. Infect. Immun. 39(1):460 (1983).

Fernie, D. S., Ripley, P. H., and Walker, P. D.. Res. Vet. Sci. 35-217 (1983).

Hudson, M. J., Alexander, T. J. L., Lysons, R. J. and Wellstead, P. D.. Brit. Vet. J. 130(2):37 (1974).

Hudson, M. J., Alexander, T. J. L., Lysons, R. J. and Prescott, J. F.. Res. Vet. Sci. 21:366 (1976).

Parizek, R., Stewart, R., Brown, K. and Blevins, D.. Vet. Med. Jul. 1985:80 (1987).

Olson, L. D., and Dayalu, K. I.. G. A. Young Swine Conference. 1987:122 (1987).

Greer, J. M. and Wannemuehler, M. J.. Infect. Immun. 57(3) (1988).

Jenkinson, S. R. and Wingar, C. R.. Vet. Rec. 109:384 (1981).

Kinyon, J. M., and Harris, D. L.. Vet. Rec. 95:219 (1974).

Stanton, T. B. and Lebo, D. F. Vet. Microbiol. 18:177 (1988).

Halter and Joens, Infection and Immunity, 56:3152-56 (Dec. 1988).

Joens, Nord, Kinyon and Egan, J. Clin. Microbiol. 15:249-52 (1982).

Stanton, et al., Intl. J. of Systematic Bacteriology; 41:50-58 (1991) Reclassification of Treponema.

Ostle, et al., Iowa State University Press, 4th Ed.; Statistics in Research; 192-194.

(List continued on next page.)

Primary Examiner—Michael G. Wityshyn
Assistant Examiner—Abdel A. Mohamed
Attorney, Agent, or Firm—Iver P. Cooper

[57] ABSTRACT

The effectiveness of parenteral vaccination of swine with Treponema hyodysenteriae preparations is increased by reducing the protein content of the Treponema hyodysenteriae cells and subcellular components in the vaccine.

10 Claims, No Drawings

OTHER PUBLICATIONS

Daniel C. Coyle, M. A. Thesis, "Investigation of the Efficacy of Various Proteinase-Treated *Serpula (Treponema) Hyodysenteriae* Vaccines" (Drake University, Sep. 1991).

Boyden et al. "Cloning and Characterization of *Treponema hyodesenteriae* Antigens and Protection in a CF-1 Mouse Model by Immunicatin with a Cloned Endoflagellar Antigen", *Infection and Immunity*, vol. 57, No. 12, pp. 3808-3815, Dec. 1989.

Lymbery et al., "Multilocus Enzyme Electrophoresis for Identification and Typing of *Treponema hyodysenteriae* and Related Spirochaetes", *Veterinary Microbiology*, 22: pp. 89-99, 1990.

Sueyoshi et al., "Diarrhea Induced by *Treponema hyodysenteriae:* a Young Chick Cecal Model for Swine Dysentery", *Infection and Immunity*, pp. 3348-3362, Oct. 1990.

Walter, Don, "Eliminatin of Swine Dysentery from two Farrow to Finish Swine Herds Utilizing Tiamulin (Denagard)", Presented at the annual meeting of the Livestock Conservation Institute, Louisville, KY, Apr. 3-5, 1990.

Anderson, et al. "Report of the Committee on Transmissible Diseases of Swine", pp. 590-591.

Duhamel et al., "Update on Prevention and Control of Swine Dysentery", G. A. Young, 1990.

Mikx, F. H. M., "Comparison of peptidase, glycosidase and esterase activities of oral and non-oral Treponema species", *Journal of General Microbiology*, 137: pp. 63-68, 1991.

Jensen, et al., "Detection and Identification of *Treponema hyodysenteriae* by Using Oligodeoxynucleotide Probes Complementary to 16S rRNA", *Journal of Clinical Microbiology*, vol. 28, No. 12, pp. 2717-2721, Dec. 1990.

Hampson, D. J., "New serogroups of *Treponema hyodysenteriae* (G, H and I)", *Veterinary Record*, 127: p. 524, 1990.

Achacha et al., "Identification of *Treponema hyodysenteriae* and *Treponema innocens* using two four-hour identification systems", *Vet. Diagn. Invest.*, 3: pp. 211-214, 1991.

Combs, et al., "Use of a whole chromosomal probe for identification of *Treponema hyodysenteriae*", *Research in Veterinary Science*, 50: pp. 286-289, 1991.

Belanger et al., "Evaluation of the An-Ident System and an Indole spot Test for the Rapid Differentiation of Porcine Treponemes", *Journal of Clinical Microbiology*, vol. 29, No. 8, pp. 1727-1729, Aug. 1991.

Joens, Lynn A., "Research Update: Swine Dysentery", Proceedings of the Historical Overview and Research Update on Enteric Diseases of Swine, Held at the Nebraska Center for Continuing Education, University of Nebraska-Lincoln, Sep. 26, 1990.

Nibbelink et al., "Susceptibility of Inbred Mouse Strains to Infection with *Serpula (Treponema) hyodysenteriae*", *Infection and Immunity*, vol. 59, No. 9, pp. 3111-3118, Sep. 1991.

Hayashi et al., "Role of Intestinal Excretion in the Effect of Subcutaneously Administered Sedecamycin on Cecal Infection Caused by *Treponema hyodysenteriae* in Mice", *Antimicrobial Agents and Chemotherapy*, vol. 35, No. 8, pp. 1601-1604, Aug. 1991.

Lysons R. J., "Microscopic agglutination: a rapid test for identification of *Treponema hyodysenteriae*", The Veterinary Record, 129: pp. 314-315, 1991.

Weber et al., "Novel Method for Measuring Growth of *Treponema hyodysenteriae* and Its Application for Monitoring Susceptibility of Clinical Isolates to Antimicrobial Agents", *Antimicrobial Agents and Chemotherapy*, vol. 35, No. 10, pp. 2012-2015, Oct. 1991.

Smith et al., "Application and evaluation of enzyme-linked immunosorbent assay and immunoblotting for detection of antibodies to *Treponema hyodysenteriae* in swine", *Epidemiol. Infect.*, 107: pp. 285-296, 1991.

Lysons et al., "A cytotoxic haemolysin from *Treponema hyodysenteriae*—a probable virulence determinant in swine dysentery", *J. Med. Microbiol.*, vol. 34, pp. 97-102, 1991.

REDUCED-PROTEIN SUBUNIT VACCINE FOR SWINE DYSENTERY

BACKGROUND OF INVENTION

1. Field of Invention

The field of this invention relates to the production of a vaccine effective against swine dysentery, a disease of swine caused by an anaerobic spirochete, Treponema hyodysenteriae.

2. Information Disclosure Statement

T. hyodysenteriae (also known as Serpula hyodysenteriae, see Stanton, et al., J. Sys. Bacteriol., 41:50-58 (1991) has been recognized as the primary etiological agent of swine dysentery (1). Although pigs infected by T. hyodysenteriae may recover and be resistant to subsequent infection by T. hyodysenteriae, efforts to induce immunity by parenteral administration of killed cells of T. hyodysenteriae have met with limited success and are generally ineffective in field use (2). Killed whole-cell T. hyodysenteriae bacterins have been developed, but often use mineral-oil base adjuvants (3) or have not involved pre-treatment of the T. hyodysenteriae cells to increase their effectiveness as a bacterin.

The use of live avirulent strains of T. hyodysenteriae as a vaccine have also been unsuccessful in protecting affected pigs (4,5). Combinations of killed T. hyodysenteriae bacterins followed by live avirulent T. hyodysenteriae vaccines have also been attempted (6).

Killed whole-cell bacterins based on T. hyodysenteriae cells produced by conventional methods have been produced and used in the field. However, the efficacy of these preparations is typically low with vaccinates reported having 50% of the incidence of swine dysentery as unvaccinated controls (7). Other preparations of killed T. hyodysenteriae cells administered as bacterins have also had limited success, with death and clinical signs of swine dysentery reported in both the vaccinated and unvaccinated animals (8).

A principal reason for the inadequate efficacy of vaccines studied to date may be the interference of other T. hyodysenteriae antigens with more functionally immunogenic antigens. A strongly immunogenic antigen which is not protective may be so much more immunogenic than a protective antigen that most of the host animal's immune response is directed against the nonprotective antigen, to the detriment of the host response to the protective antigen. In other words, nonfunctional antigens (those which do not provide disease resistance) may compete with functional antigens. Other reasons for this may be that the functional antigen is concealed by the nonfunctional antigen (sterically) or that antibody produced to the nonprotective antigen blocks the protective antigen which is thus not processed by the host immune system.

Treponema hyodysenteriae is a helical anaerobic spirochaete. As recently as 1988, researchers declared that "little information is available regarding the physiology, cell biochemistry and nutrition" of this organism (13).

Lipooligosaccharides (LOS) have been extracted with hot phenol-water from the other membranes of T. hyodysenteriae serotypes 1 through 7 (14). These LOSs have been used as an antigenic reagent in an enzyme-linked immunosorbent assay for the detection of antibodies to T. hyodysenteriae antigens (16). This left unresolved the question of whether the LOSs were protective antigens suitable for vaccine use. Moreover, some reports suggested that treponemal lipopolysaccharide was toxic.

No admission is made that any of the references cited herein is prior art. The discussion of the references is based solely on their published content and is not binding on Applicants.

SUMMARY OF INVENTION

This invention is based on a method of increasing the effectiveness of killed preparations of T. hyodysenteriae. The method is practiced by the parenteral administration of a vaccine or bacterin containing as the active immunizing agent T. hyodysenteriae cells and subcellular components which have been pretreated to reduce the protein content of the T. hyodysenteriae components. Whole cells which may be grown in any of several recognized media and under conditions recognized in prior art are treated to reduce the amount of protein from the T. hyodysenteriae cells and subcellular components present in the preparation. This reduced-protein preparation is then administered by parenteral injection to swine, preferably before they are infected with T. hyodysenteriae.

The equivalent of $5 \times 10^9$ killed cells of T. hyodysenteriae treated to reduce the protein content of the bacterin or vaccine is sufficient to reduce death and morbidity due to swine dysentery caused by T. hyodysenteriae infection. The protection against both death and morbidity due to swine dysentery caused by T. hyodysenteriae infection which is provided by the reduced-protein vaccine or bacterin is superior to that noted with similar preparations of killed T. hyodysenteriae cells or subcellular components which have not been pretreated to reduce the protein content.

The exact nature of the antigen immune response is unknown, although a systemic response to the LOS- or LPS-like component of T. hyodysenteriae cells by both the cellular and humoral immune systems of the swine is likely to be involved. This immune response to the LPS-like component of T. hyodysenteriae cells is likely to be enhanced by the reduction in extraneous proteins from T. hyodysenteriae cells and other sources which may interfere in the elicitation of a specific immune response to the LPS-like component of T. hyodysenteriae (9).

DETAILED DESCRIPTION OF THE PREFERRED EMBODIMENTS

The treponema outer membrane may be extracted with sodium-N-lauryl sarcosinate (sarcosine) or Triton X-100. Other chaotropic agents may also be employed. The apparent molecular weights of the predominant proteins in the range 22–49 kDa in Triton X-100 preparations of T. hyodysenteriae B204, as determined from polyacrylamide gels stained with Coomassie Blue after SDS-PAGE, were as follows (15):

44.9±1.4
43.6±1.2
42.3±1.3
40.8±1.6
38.7±1.4
35.9±1.3
33.7±1.6
31.6±1.5
30.0±0.9
29.0±1.1
26.6±0.9

23.6±0.4

There is an OM component in the 14–19 kDa range that does not stain with coomassie blue but can be silver-stained.

The majority of the proteins in the 22.5 to 46.5 kDa range could be surface labeled, but there was no detectable label in the 14–19 kDa range. Immunoblot analysis of variously treated OM preparations revealed that the antigenic epitopes were resistant to proteinase-K, beta-glucuronidase, neuraminidase and trypsin, but sensitive to periodate, suggesting that they were carbohydrate in nature (15).

Some components of the lipopolysaccharides of *T. hyodysenteriae* have been tentatively identified by gas-liquid chromatography, based on their retention times. The sugars include fucose, galactose, glucose, glucosamine, heptose, mannose, rhamnose and a thiobarbitaric acid-reactive component 2-Keto-3-deoxyoctonate. The fatty acids included myristic acid, 13-methyl-myristic acid, and 3-hydroxy-hexadecanoic acid.

The outer membrane also includes endotoxins which can be extracted with trichloroacetic acid or with butanol-water (a). The endotoxins are about 11% protein.

In one embodiment, the present invention is directed to a vaccine preparation derived from *T. hyodysenteriae* in which the protein content has been substantially reduced, so that a statistically significant reduction in morbidity (bloody scours) is observed in pigs challenged after vaccination. Preferably, the product contains less than 1 µg/ml intact protein of 5–8,000 daltons or above. Generally speaking, if the preferred product is analyzed by SDS-PAGE, silver staining of the gel will be unable to detect immunogenic >5,000 daltons.

Treponema hyodysenteriae strains (both virulent and avirulent) are available from United States and foreign culture depositories and from private culture collections. Several different serotypes (currently seven) of T. hyodysenteriae are known to exist and to cause swine dysentery in susceptible animals. Methods for the isolation of T. hyodysenteriae have been described in the literature (10). Suitable isolates include strain number 31212 (or B204) of serotype 2 from the American Type Culture Collection (a, 11). However, any isolate of T. hyodysenteriae capable of causing disease in swine is suitable for the practice of this invention.

Treponema hyodysenteriae cells may be grown in either solid or liquid growth media. Trypticase soy broth (TSB) with 7.5% horse serum (HS) 0.5% yeast extract, VPI anaerobe salts (12) and 0.05% L-cysteine is suitable for preparing T. hyodysenteriae cells for the practice of this invention, although other suitable media are known in the literature (13). T. hyodysenteriae cells are grown anaerobically or microaerophillically in reduced oxygen atmospheres at temperatures of 35°–40° C. (13). After growth, T. hyodysenteriae cells may be killed by standard methods such as formalin, merthiolate or heat treatment (although merthiolate is preferred) and collected by centrifugation or ultrafiltration. The T. hyodysenteriae cells may also be killed by the process of lysing the cells which may be performed by physical means such as pressure treatment or sonication or by changes in the pH or tonicity of the surrounding medium. The extraction of the outer membrane is not necessary, but is permissible.

After suitable T. hyodysenteriae cells are prepared and lysed, they are treated to reduce the protein content of the preparation. Such a reduction in the protein content may be accomplished by treatment with protein-degrading enzymes such as proteinase-K. It should be understood that many protein-degrading enzymes are known in the literature and any enzyme or physical or chemical treatment which results in a significant reduction in the protein content of the preparation (without adversely affecting immunogenicity of the product) is suitable for the practice of this method. The specific conditions of temperature, pH and other physical values under which the protein-reduction occurs is dependent on the enzyme or protein-reducing system employed. For example, if proteinase-K is used, a commercial proteinase-K preparation is added to the cell and lysed cell suspension which is then incubated at 56° C. for two hours and 37° C. for an additional twelve hours.

The reduced-protein suspension is preferably derived from at least about $5 \times 10^9$ T. hyodysenteriae cells per dose comprises the vaccine, although levels of antigen equal to at least $1 \times 10^{10}$ T. hyodysenteriae cells per does are more preferred. This preparation may be mixed with various adjuvant preparations known in the literature such as mineral oils, metabolizable organic oils, emulsifiers or metal salts to enhance the effectiveness of the vaccine. While mineral oils are not preferred, as they are potential carcinogens and may also cause adverse reactions, they may be used if desired. It should be understood that while the use of various adjuvant preparations may enhance the effectiveness of this or any vaccine their use is not necessary to the practice of this method.

The vaccine prepared by the practice of this method is administered to swine parenterally, generally by intramuscular or subcutaneous injection. The vaccine is most effective if administered to swine which are otherwise healthy and not already showing symptoms of swine dysentery. The vaccine is preferably administered in a series of at least two doses separated by two-three weeks, but other immunization schedules may be efficacious and may be determined by conventional means.

The method of this invention is further illustrated by the following experimental examples.

EXAMPLE 1

A strain of Treponema hyodysenteriae serotype 2 isolated from swine and designated as B-204 was grown in pure culture in a liquid medium consisting of trypticase soy broth supplemented with 5.0% horse serum (HS) 0.5% yeast extract, VPI anaerobe salts (12) and 0.05% L-cysteine. This culture was grown at 39° C. in an atmosphere of 10% $CO_2$, 10% $H_2$ and 80% $N_2$ for 12 hours by which time the majority of the growth of T. hyodysenteriae had ceased. The T. hyodysenteriae cells were then killed by the addition of 1:10,000 merthiolate. These killed cells were then collected by centrifugation at 20,000×g for 45 minutes and resuspended in sterile 0.85% saline after which they were lysed by the application of pressure in a French pressure cell (5,000 psi) and the cell membranes of the lysed T. hyodysenteriae cells collected by centrifugation of the lysate at 100,000×g for 2 hours. This membrane material was resuspended in sterile phosphate-buffered 0.85% saline (pH 7.2) and treated with protease type XI-S (proteinase-K) at 56° C. for 2 hours followed by further incubation at 37° C. for 12 hours. After protease treatment the *T. hyodysenteriae* subcellular components were stored at 4° C. and comprised the concentrated vaccine. The concentrated vaccine was mixed with 25% Freund's Incomplete Adjuvant (FIA) to form a waterin-oil-in-water emulsion for injection into test animals. Similar preparations were made with whole-cell untreated *T. hyodysenteriae* cells in FIA and untreated *T. hyodysenteriae* cell membranes in FIA to test the effectiveness of the protein-reduction method.

The reduced-protein preparation were tested for outer membrane protein content by sodium-dodecyl-sulfate polyacrylamide gel electrophoresis (SDS-PAGE) assay with untreated *T. hyodysenteriae* membranes as a control. For a suitable protocol, see Merrill, et al., Science, 211:1437 (1981). The untreated *T. hyodysenteriae* membranes had many protein bands evident in the gel after silver staining while only three protein bands could be noted in the reduced-protein *T. hyodysenteriae* membranes. This indicates that the majority of the native or natural *T. hyodysenteriae* membrane proteins were reduced by the proteinase K treatment to a level below the ability of the SDS-PAGE/silver stain assay to detect specific proteins.

Sixteen SPF (Specific Pathogen Free) swine from a herd known to be free of swine dysentery were weighed and used to test these preparations. Pigs were randomly assigned to groups. Four pigs were given the equivalent of $4\times10^{10}$ *T. hyodysenteriae* cells per dose of reduced-protein vaccine in FIA in two doses two weeks apart. Four pigs were given whole cell T. hyodystneriae untreated by proteinase K in doses of $2\times10^{10}$ T. hyodysenteriae cells per dose in FIA in two doses two weeks apart. Four pigs were given membranes untreated by proteinase K in the equivalent of $4\times10^{10}$ T. hyodysenteriae cells per dose of T. hyodysenteriae vaccine in FIA in two doses two weeks apart. These experimental groups are outlined in Table 1.

TABLE 1

Experimental Groups of Treatment

| Group | Number of pigs | Vaccine | Doses |
|---|---|---|---|
| 1 | 4 | 2 X Reduced-Protein Membrane | 2 doses 2 weeks apart |
| 2 | 4 | 1 X Whole Untreated Cells | 2 doses 2 weeks apart |
| 3 | 4 | 2 X Untreated Membranes | 2 doses 2 weeks apart |
| 4 | 4 | None (controls) | None |

Ten days after the second vaccination all experimental pigs were fasted for 24 hours, re-weighed and challenged with $1.69\times10^{11}$ actively-growing, motile *Treponema hyodysenteriae* cells by oral inoculation. Unvaccinated control pigs were in continuous contact with the vaccinated pigs both before and after challenge. All pigs were observed daily for 21 days after challenge and any signs of swine dysentery (eg. bloody diarrhea) were recorded. At the end of the 21 day observation period, all surviving pigs were re-weighed, sacrificed and necropsied. Samples were taken of the intestinal contents of the spiral colon and the cecum for re-isolation of Treponema hyodysenteriae. Lesions typical of swine dysentery were recorded during necropsy.

The results of the post-challenge observations of all groups are outlined in Table 2.

TABLE 2

Post-Challenge Observations of-Vaccinated and Control Pigs

| Group | Treatment | # Pigs | MID Total | MID Scour | ADG | Mortality | T. hyo* |
|---|---|---|---|---|---|---|---|
| 1 | Reduced-Protein | 4 | 0.0% | 0.0% | 0.98 lb/day | 0% | 0/4 |
| 2 | Whole-Cell | 4 | 7.2% | 0.0% | 0.47 lb/day | 0% | 1/4 |
| 3 | Membrane | 4 | 16.1% | 16.1% | 0.87 lb/day | 0% | 3/4 |
| 4 | CONTROL | 4 | 33.1% | 21.7% | 0.94 lb/day | 0% | 2/4 |

*Treponema hyodysenteriae reisolated from feces. Number of pigs with Treponema hyodysenteriae/number of pigs in group.

Total morbidity, all observed symptoms. Equals (total number of days with symptoms/total number of pig days) × 100.

Morbidity with scours only. Difference from total morbidity is chiefly weakness and quantness counted in the total MID column.

Results

Bloody diarrhea typical of swine dysentery (MID scour) was observed in unvaccinated control animals on 21.7% of the daily observations. Bloody diarrhea was also noted in 16.1% of the daily observations of pigs receiving a vaccine consisting of Treponema hyodysenteriae membranes which had not been treated by the protein reduction method. Pigs receiving whole cell untreated Treponema hyodysenteriae had no bloody diarrhea. None of the four pigs receiving reduced-protein T. hyodysenteriae vaccine had bloody diarrhea typical of swine dysentery. These data clearly demonstrate that the reduced-protein T. hyodysenteriae vaccine was superior in reducing the incidence of bloody scours typical of swine dysentery as compared to unvaccinated control pigs. Further, the protection against bloody diarrhea was significantly greater than that noted in untreated whole-cell Treponema hyodysenteriae vaccines prepared according to reported methods (7).

This protection also extended to increased average daily weight gains in pigs receiving reduced-protein T. hyodysenteriae vaccine (0.98 lbs/day) as compared to pigs receiving classical killed, untreated whole-cell T. hyodysenteriae vaccine (0.47 lb/day), although controls were not as severely affected in this test.

Treponema hyodysenteriae was re-isolated after challenge from two of four unvaccinated control pigs (50%) and one of four pigs receiving classical killed, untreated whole-cell T. hyodysenteriae vaccine (25). However, T. hyodysenteriae was not reisolated from any of the four pigs receiving reduced-protein T. hyodysenteriae vaccine.

These data clearly demonstrate that a reduced-protein T. hyodysenteriae vaccine made according to the method in this claim protects pigs vaccinated with such a preparation against the symptoms of swine dysentery (bloody diarrhea), weight loss due to T. hyodysenteriae infection and re-isolation of T. hyodysenteriae. Further, this protection is notably superior not only to unvaccinated control pigs but also to killed whole cell or membrane T. hyodysenteriae vaccines made according to the prior art. The method of reducing the protein content of T. hyodysenteriae vaccines prior to administration to swine clearly results in enhanced protection of swine to swine dysentery due to Treponema hyodysenteriae infection which is superior to that heretofore available.

Example 2

A strain of Treponema hyodysenteriae serotype 2 isolated from swine and designated as B-204 was grown in pure culture in a liquid medium consisting of trypticase soy broth supplemented with 7.5% horse serum (HS) 0.5% yeast extract, VPI anaerobe salts (12) and 0.05% L-cysteine. This culture was grown at ⇌° C. in an atmosphere of 5% $CO_2$, 10% $H_2$ and 85% $N_2$ for 8 hours by which time the majority of the growth of T. hyodysenteriae had ceased. The T. hyodysenteriae cells were then killed by the addition of 1:10,000 merthiolate. These killed cells were then collected by centrifugation at $20,000 \times g$ for 45 minutes and resuspended in sterile 0.85% saline after which they were lysed by the application of pressure in a French pressure cell (5,000 psig) and the cell membranes of the lysed T. hyodysenteriae cells collected by centrifugation of the lysate at $100,000 \times g$ for 2 hours. This membrane material was resuspended in sterile Phosphate-buffered 0.85% saline (pH 7.2) and treated with protease type XI-S (proteinase-K) at 56° C. for 2 hours followed by further incubation at 37° C. for 12 hours. After protease treatment the T. hyodysenteriae subcellular components were stored at 4° C. and comprised the concentrated vaccine. The concentrated vaccine was mixed with 25% Freund's Incomplete Adjuvant (FIA) to form a water-in-oil-in-water emulsion for injection into test animals. Similar preparations were made with whole-cell untreated T. hyodysenteriae cells in FIA and untreated T. hyodysenteriae cell membranes in FIA to test the effectiveness of the protein-reduction method.

The reduced-protein preparation was tested for outer membrane protein content by sodium-dodecyl-sulfate polyacrylamide gel electrophoresis (SDS-PAGE) assay with untreated T. hyodysenteriae membranes as a control. The untreated T. hyodysenteriae membranes had many protein bands evident in the gel after silver staining while only three protein bands could be noted in the reduced-protein T hyodysenteriae membranes. This indicates that the majority of the native or natural T. hyodysenteriae membrane proteins were reduced by the proteinase K treatment to a level below the ability of the SDS-PAGE/silver stain assay to detect specific proteins.

Thirty SPF (Specific Pathogen Free) swine from a herd known to be free of swine dysentery were weighed and used to test these preparations. Pigs were randomly assigned to groups. Six pigs were given the equivalent of $2 \times 10^{10}$ T. hyodysenteriae cells per does of reduced-protein vaccine in FIA in two doses three weeks apart. Six pigs were given whole cell T. hyodysenteriae untreated by proteinase K in doses of $2 \times 10^{10}$ T. hyodysenteriae cells per dose in FIA in two doses three weeks apart. Six pigs were given membranes untreated by proteinase K in the equivalent of $2 \times 10^{10}$ T. hyodysenteriae cells per dose of T. hyodysenteriae vaccine in FIA in two doses three weeks apart. To test the dose/response of the reduced-protein vaccine, groups of two pigs each were given 4X, ½X or ¼X the dose of reduced-protein vaccine in FIA in two doses three weeks apart. All experimental animals were housed together in one large room and were fed and handled identically. These experimental groups are outlined in Table 3.

Table 3
Experimental Groups and Treatments

| Group | Number of Pigs | Vaccine |
|---|---|---|
| 1 | 2 | 4 X Reduced-Protein Membranes |
| 2 | 6 | 1 X Reduced-Protein Membranes |
| 3 | 2 | ½ X Reduced-Protein Membranes |
| 4 | 2 | ¼ X Reduced-Protein Membranes |
| 5 | 6 | 1 X Whole Untreated Cells |
| 6 | 6 | 1 X Untreated Membranes |
| 7 | 6 | None (controls) |

In each of groups 1-6, two doses of the vaccine were administered 3 weeks apart.

Eight days after the second vaccination all experimental pigs were fasted for 24 hours, re-weighed and challenged with $5 \times 10^{10}$ actively-growing, motile Treponema hyodysenteriae cells by oral inoculation. This challenge was repeated the next day (day nine after the second vaccination). As all pigs were housed together, the unvaccinated control pigs were in continuous contact with the vaccinated pigs both before and after challenge. All pigs were observed daily for 25 days after the second challenge and any signs of swine dysentery (eg. bloody diarrhea) were recorded. At the end of the 25 day observation period, all surviving pigs were re-weighed, sacrificed and necropsied. Samples were taken of the intestinal contents of the spiral colon, ileocecal orifice and the cecum for re-isolation of Treponema hyodysenteriae. Lesions typical of swine dysentery were recorded during necropsy.

The results of the post-challenge observations of all groups are outlined in Table 4.

TABLE 4

Post-Challenge Observations of Vaccinated and Control Pigs

| Vaccine | # Pigs | # Dead | # Bloody Scours | MID* Bloody Scours | MID Scours (Other) | T. hyo Reisolated | ADG** lb/day |
|---|---|---|---|---|---|---|---|
| Protein-reduced membrane 4 X | 2 | 0 | 0 (0%) | 0% (0%) | 8.0% | 1(50%) | 0.86 |
| Protein-reduced membrane 1 X | 6 | 0 | 0 (0%) | 0% (0%) | 0.0% | 0(0%) | 0.91 |
| Protein-reduced membrane ½ X | 2 | 0 | 0 (0%) | 0% (0%) | 0.0% | 0(0%) | 0.70 |
| Protein-reduced | 2 | 1 | 1 (50%) | 5.4% (50%) | 0.0 | 1(50%) | 0.40 |

TABLE 4-continued

Post-Challenge Observations of Vaccinated and Control Pigs

| Vaccine | # Pigs | # Dead | # Bloody Scours | MID* Bloody Scours | MID Scours (Other) | T. hyo Reisolated | ADG** lb/day |
|---|---|---|---|---|---|---|---|
| membrane ¼ X | | | | | | | |
| Whole Cell | 6 (17%) | 1 | 2 (33%) | 7.5% | 8.8% | 3(50%) | 0.63 |
| Membrane | 6 (0%) | 0 | 5 (83%) | 16.7% | 4.7% | 5(83%) | 0.39 |
| Control | 6 (17%) | 1 | 5 (83%) | 29.6% | 6.3% | 3(50%) | 0.37 |

*Morbidity Incidence and Duration. Equals (number of days with bloody diarrhea/total number of days since challenge to sacrifice or death) × 100.
Morbidity Incidence and Duration. Equals (number of days with diarrhea other than bloody diarrhea/total number of days since challenge to sacrifice or death) × 100.
**Average Daily Weight Gain. Equals (weight at time of sacrifice or death minus weight at time of challenge)/number of days challenge to sacrifice or death. In pounds gained per day.

Results

Bloody diarrhea typical of swine dysentery was observed in 5/6 (83%) of the unvaccinated control animals. Bloody diarrhea was also noted in 5/6 (83%) of pigs receiving a vaccine consisting of Treponema hyodysenteriae membranes which had not been treated by the protein reduction method. Two of six (33%) pigs receiving whole cell untreated Treponema hyodysenteriae had bloody diarrhea. However, none of the ten pigs receiving reduced-protein T. hyodysenteriae vaccine at either the 4X, 1X or ½X doses had bloody diarrhea typical of swine dysentery. When the reduced-protein T. hyodysenteriae vaccine was reduced to ¼ of a dose, one of the two pigs receiving this vaccine had bloody diarrhea, indicating a dose-response to the reduced-protein T. hyodysenteriae vaccine. These data clearly demonstrate that the reduced-protein T. hyodysenteriae vaccine was superior in reducing the incidence of bloody scours typical of swine dysentery as compared to unvaccinated control pigs. Further, the protection against bloody diarrhea was significantly greater than that noted in untreated whole-cell Treponema hyodysenteriae vaccines prepared according to the previous art (7).

This protection also extended to increased average daily weight gains in pigs receiving reduced-protein T. hyodysenteriae vaccine (0.91 lbs/day) as compared to untreated controls (0.37 lbs/day) or pigs receiving classical killed, untreated whole-cell T. hyodysenteriae vaccine (0.63 lb/day). Death loss was reduced 100% in pigs receiving reduced-protein T. hyodysenteriae vaccine as compared to deaths noted in pigs receiving both untreated whole-cell vaccine and no vaccine (controls).

Pigs receiving 1X reduced protein vaccine (group 3) were protected against challenge as measured by average daily weight gain ($p=0.065$) and reduced morbidity (Bloody Scours) ($p=0.007$). Pigs given ½X reduced protein vaccine (group 4) were protected against challenge as measured by reduced morbidity (Bloody Scours) ($p=0.088$) but not average daily weight gain ($p=0.317$). Pigs given ¼X reduced protein vaccine (group 5) were not significantly protected against challenge as measured by reduced morbidity (Bloody Scours) ($p=0.241$) or average daily weight gain ($p=0.739$). All analysis was by the Kruskal-Wallis one-way analysis of variance. Thus, the reduced protein vaccine offers statistically significant protection at concentration of at least about ½X. The product contained less than 1 μg/ml protein of 5–8,000 Da or above when used.

Treponema hyodysenteriae was re-isolated after challenge from three of six unvaccinated control pigs (50%) and three of six pigs receiving classical killed, untreated whole-cell T. hyodysenteriae vaccine (50%). However, T. hyodysenteriae was only reisolated from one of ten pigs receiving 4X, 1X or ½X reduced-protein T. hyodysenteriae vaccine.

These data clearly demonstrate that a reduced-protein T. hyodysenteriae vaccine made according to the method in this claim protects pigs vaccinated with such a preparation against the symptoms of swine dysentery (death loss, bloody diarrhea), weight loss due to Treponema hyodysenteriae infection and re-isolation of Treponema hyodysenteriae. Further, this protection is notably superior not only to unvaccinated control pigs but also to killed whole cell or membrane T. hyodysenteriae vaccines made according to the prior art. The method of reducing the protein content of T. hyodysenteriae vaccines prior to administration to swine clearly results in enhanced protection of swine to swine dysentery due to Treponema hyodysenteriae infection which is superior to that heretofore available.

Tables 5, 6 and 7 further show the advantage of the Proteinease K digest over whole cell lysate and endotoxin preparations. In Table 5, we see a higher cecal weight and increased freedom from gross lesions. Table 6 reveals that the number of T. hyodysenteriae recovered from vaccinated mice following challenge is most reduced by the PK digest. Finally, Table 7 shows a tendency toward a lower number of colony forming units.

TABLE 5

Protection of Mice from Infection with Treponema hyodysenteriae Following Immunization

| Treatment | Animal no. | Clinical signs[a] | cecal weight[b] | dark field microscopy[c] |
|---|---|---|---|---|
| Saline | 1 | NGL | 0.24 | N.D. |
| | 2 | XM | 0.19 | +2 |
| | 3 | NGL | 0.30 | N.D. |
| | 4 | XM&At | 0.13 | +2 |
| | 5 | XM&At | 0.10 | +3 |
| | 6 | XM | 0.23 | +1 |
| | 7 | NGL | 0.32 | N.D. |
| | | | Avg 0.22 ± 0.08 | |
| Whole Cell Lysate[d] | 8 | NGL | 0.18 | N.D. |
| | 9 | NGL | 0.24 | N.D. |
| | 10 | XM | 0.13 | +2 |
| | 11 | XM | 0.18 | N.D. |
| | 12 | NGL | 0.26 | +1 |
| | 13 | XM | 0.18 | +2 |
| | 14 | NGL | 0.20 | N.D. |
| | | | Avg 0.20 ± 0.04 | |

TABLE 5-continued

Protection of Mice from Infection with
Treponema hyodysenteriae Following Immunization

| Treatment | Animal no. | Clinical signs[a] | cecal weight[b] | dark field microscopy[c] |
|---|---|---|---|---|
| Endotoxin[e] | 15 | XM | 0.23 | +1 |
| | 16 | NGL | 0.23 | N.D. |
| | 17 | NGL | 0.24 | N.D. |
| | 18 | NGL | 0.36 | N.D. |
| | 19 | XM | 0.20 | +1 |
| | 20 | NGL | 0.22 | N.D. |
| | 21 | XM | 0.21 | N.D. |
| | | | Avg 0.24 ± 0.05 | |
| PK Digest[f] | 22 | NGL | 0.18 | N.D. |
| | 23 | NGL | 0.24 | N.D. |
| | 24 | NGL | 0.22 | N.D. |
| | 25 | NGL | 0.29 | N.D. |
| | 26 | NGL | 0.27 | N.D. |
| | 27 | NGL | 0.22 | N.D. |
| | | | Avg 0.24 ± 0.04 | |

[a]Clinical signs of the disease were defined as the presence of excess Intraluminal mucus (XM), atrophy of the cecum (At) or no gross lesions (NGL). Two weeks following the last immunization, mice were challenged with $5 \times 10^6$ T. hyodysenteriae B204 on two consecutive days and then sacrificed 10 days later.
[b]The weight of each cecum is expressed in grams.
[c]Cecal contents were observed by dark field microscopy for the presence of spirochetes and given a relative score from +1 to +3 if spirochetes were observed or "N.D." if none were detected.
[d]Mice were interperitoneally immunized three times (two weeks apart) with 50 μg (protein content) of a whole cell lysate prepared from T. hyodysenteriae B204.
[e]Mice were immunized (ip) three times with 50 μg of endotoxin (butanol/water extract) from T. hyodsenteriae B204.
[f]Mice were immunized (ip) three times with a proteinase K digested whole cell lysate (equivalent to 50 μg of the whole cell lysate).

TABLE 6

Number of Treponema hyodysenteriae recovered from vaccinated mice following Challenge.

| Treatment[b] | n[c] | CFU[d] |
|---|---|---|
| Saline | 7 | $4.1 \pm 2.2 \times 10^6$ |
| Whole Cell Lysate | 7 | $2.5 \pm 1.1 \times 10^6$ |
| Endotoxin | 7 | $1.1 \pm 0.5 \times 10^6$ |
| Proteinase K Digest | 6 | $5.0 \pm 0.5 \times 10^5$ |

[a]Mice challenged on two consecutive days with $5 \times 10^6$ T. hyodysenteriae and sacrificed 10 days later.
[b]Mice were immunized as described for Table 1.
[c]Number of mice per group.
[d]Colony forming units (CFU) of T. hyodysenteriae per gram of cecal tissue.

Colony forming units of T. hyodysenteriae recovered from infected mice.

| Treatment | No. | DF[b] | Culture | CFU[d] |
|---|---|---|---|---|
| Saline | 1 | − | + | $2.1 \times 10^4$ |
| | 2 | ++ | + | $5.3 \times 10^6$ |
| | 3 | − | + | $1.7 \times 10^4$ |
| | 4 | ++ | + | $6.9 \times 10^6$ |
| | 5 | +++ | + | $1.6 \times 10^7$ |
| | 6 | + | + | $7.0 \times 10^5$ |
| | 7 | − | + | $9.4 \times 10^4$ |
| Whole Cell Lysate[d] | 8 | − | + | $1.1 \times 10^5$ |
| | 9 | − | + | $8.3 \times 10^4$ |
| | 10 | ++ | + | $2.5 \times 10^6$ |
| | 11 | − | + | $5.3 \times 10^6$ |
| | 12 | + | + | $7.7 \times 10^6$ |
| | 13 | ++ | + | $1.4 \times 10^6$ |
| | 14 | − | + | $1.0 \times 10^5$ |
| Endotoxin | 15 | + | + | $1.3 \times 10^6$ |
| | 16 | − | − | 0 |
| | 17 | − | + | $8.3 \times 10^4$ |
| | 18 | − | + | $<1.0 \times 10^4$ |
| | 19 | + | + | $4.0 \times 10^6$ |
| | 20 | − | + | $1.8 \times 10^5$ |
| | 21 | − | + | $2.0 \times 10^6$ |
| Proteinase K Digest | 22 | − | + | $<1.0 \times 10^4$ |
| | 23 | − | + | $<1.0 \times 10^4$ |
| | 24 | − | + | $2.3 \times 10^4$ |
| | 25 | − | + | $<1.0 \times 10^4$ |
| | 26 | − | + | $3.1 \times 10^6$ |
| | 27 | − | + | $4.5 \times 10^4$ |

[a]Mice were vaccinated as described for Table 1.
[b]Presence (+) or absence (−) of spirochetes in cecal contents as determined by dark field microscopy (DF).
[c]Cecal content were directly cultured on blood agar media for the detection of B-hemolytic spirochetes.
[d]Ceca were excised from each mouse, weighed, and homogenized. The homogenate was serially diluted and the number of colony forming units (CFU) of T. hyodysenteriae per gram cecum was determined.

References Cited a. Glock, et al., U.S. Pat. No. 4,100,272.
b. Goodnow, U.S. Pat. No. 4,152,413.
c. Harris, U.S. Pat. No. 4,152,414.
d. Harris and Goodnow, U.S. Pat. No. 4,152,415.
e. Hasegawa, U.S. Pat. No. 4,794,105.
f. Parizek, U.S. Pat. No. 4,758,517.
g. Lysons, U.S. Pat. No. 4,748,019.
h. Glock, U.S. pat. No. 4,203,968.
i. Gabe, EP 282,965.
j. Coloe, WO88/04555.
k. Parizek, EP 201,796.
1. Harris, D.L., Glock, R.D., Christiansen, C. R. and Kinyon, J. M.. Vet. Med. Small Animal Clin. 67:61 (1972).
2. Joens, L. A., Whipp, S. C., Glock, R. D., and M. E. Neussen. Infect. Immun. 39(1):460 (1983).
3. Fernie, D.S., Ripley, P. H., and Walker, P. D.. Res. Vet. Sci. 35-217 (1983).
4. Hudson, M.J., Alexander, T. J. L., Lysons, R. J. and Wellstead, P. D.. Brit. Vet. J. 130(2):37 (1974).
5. Hudson, M. J., Alexander, T. J. L., Lysons, R. J. and Prescott, J. F.. Res. Vet. Sci. 21:366 (1976).
6. Lysons, R. J. International Patent No. WO 85/03875. (Mar., 1985).
7. Parizek, R., Stewart, R., Brown, K. and Blevins, D. Vet. Med. Jul. 1985:80 (1985).
8. Olson, L. D., and Dayalu, K. I.. G. A. Young Swine Conference. 1987:122 (1987).
9. Greer, J. M. and Wannemuehler, M. J.. Infect. Immun. 57(3):717(1988).
10. Jenkinson, S. R. and Wingar, C. R.. Vet. Rec. 109:384 (1981).
11. Kinyon, J. M., and Harris, D. L.. Vet. Rec. 95:219 (1974).
12. Holdeman, L. V., Cato, E. P., and Moore, W. E. C.. Anaerobe laboratory manual, 4 th Ed. Virginia Polytechnic Institute (1977).
13. Stanton, T. B. and Lebo, D. F. Vet. Microbial. 18:177 (1988).
14. Halter, M. and Joens, L.A., Infection and Immunity, 56:3152-56 (Dec. 1988).
15. Wannemuehler, M.J., Hubbard, R.D. and Greer, J.M., Infection and Immunity, 56:3032-39 (Dec. 1988).
16. Joens, L.A., Nord, L.A., Kinyon, J.M., and Egan, D.J., J. Clin. Microbiol. 15:249-52 (1982).

We claim:

1. A vaccine comprising an immunogenic preparation derived from Treponema hyodysenteriae cells and having a substantially reduced intact outer membrane protein content relative to said cells, said vaccine providing a statistically significant reduction in morbidity due to Treponema hyodysenteriae infection in pigs immunized with said vaccine prior to said infection, and a pharmaceutically acceptable carrier.

2. The vaccine of claim 1, said vaccine being further characterized in that it provides a greater reduction in morbidity than that provided by a killed whole cell Treponema hyodysenteriae vaccine.

3. The vaccine of claim 1, wherein the protein content was enzymatically reduced.

4. The vaccine of claim 3, wherein the enzyme has the characteristic substrate specificity of proteinase K.

5. The vaccine of claim 1, wherein the preparation is derived from an outer membrane extract of Treponema hyodysenteriae cells.

6. A method of increasing the resistance of swine to Treponema hyodysenteriae which comprises administering to susceptible swine a vaccinologically effective amount of a vaccine according to claim 1.

7. A method of increasing the resistance of swine to *Treponema hyodysenteriae* which comprises administering to susceptible swine a vaccinologically effective amount of a vaccine according to claim 2.

8. A method of increasing the resistance of swine to *Treponema hyodysenteriae* which comprises administering to susceptible swine a vaccinologically effective amount of a vaccine according to claim 3.

9. A method of increasing the resistance of swine to *Treponema hyodysenteriae* which comprises administering to susceptible swine a vaccinologically effective amount of a vaccine according to claim 4.

10. A method of increasing the resistance of swine to *Treponema hyodysenteriae* which comprises administering to susceptible swine a vaccinologically effective amount of a vaccine according to claim 5.

* * * * *